US006385281B1

(12) United States Patent
Ozawa et al.

(10) Patent No.: US 6,385,281 B1
(45) Date of Patent: May 7, 2002

(54) FLUORESCENT X-RAY ANALYZING METHOD AND APPRARTUS

(75) Inventors: Tetsuya Ozawa; Kazuhiko Omote; Jimpei Harada, all of Tokyo (JP)

(73) Assignee: Rigaku Corporation, Tokyo (JP)

( * ) Notice: Subject to any disclaimer, the term of this patent is extended or adjusted under 35 U.S.C. 154(b) by 0 days.

(21) Appl. No.: 09/657,980

(22) Filed: Sep. 8, 2000

(30) Foreign Application Priority Data

Sep. 9, 1999 (JP) .......................................... 11-256367

(51) Int. Cl.⁷ ............................................. G01N 23/223
(52) U.S. Cl. ......................................................... 378/45
(58) Field of Search ..................................... 378/44–50

(56) References Cited

U.S. PATENT DOCUMENTS 5,497,407 A * 3/1996 Kamatsu ...................... 378/45
6,028,911 A * 2/2000 Kavahara ..................... 378/45

* cited by examiner

Primary Examiner—Craig E. Church
(74) Attorney, Agent, or Firm—Wenderoth, Lind & Ponack, L.L.P.

(57) ABSTRACT

The present invention provides a new fluorescent X-ray analyzing method and an apparatus thereof which is capable of performing, with great precision, quantitative analysis and qualitative analysis for an atomic species generating fluorescent X-rays of not only a symmetrical energy spectrum but also an asymmetrical energy spectrum, wherein fluorescent X-rays generated from a sample by irradiation of X-rays or particle beams are measured as an energy spectrum, and profile fitting to the measured energy spectrum is performed by using an asymmetrical profile function which can express a symmetrical and an asymmetrical energy spectrum in accordance with an asymmetrical factor.

20 Claims, 12 Drawing Sheets

FLUORESCENT X-RAY ANALYZING METHOD AND APPRARTUS

BACKGROUND OF THE INVENTION

1. Field of the Invention

The present invention relates to a fluorescent X-ray analyzing method and an apparatus thereof. More particularly, the present invention relates to a new fluorescent X-ray analyzing method and a new fluorescent X-ray analyzing apparatus which can perform profile fitting to an energy spectrum with a high degree of freedom and with great precision.

2. Description of the Related Art

Conventionally, for quantitative analysis or qualitative analysis of a sample, there is used a fluorescent X-ray analyzing method which employs fluorescent X-rays generated from the sample by irradiation of X-rays (primary X-rays) or particle beams such as neutron beams or electron beams. This fluorescent X-ray analyzing method can be roughly divided into a wavelength dispersive type and an energy dispersive type.

In the wavelength dispersive type, fluorescent X-rays generated from a sample are adjusted into a parallel beam by a Soller slit, and then it is made an X-ray spectrum dispersed for respective wavelengths by a dispersion system provided with an spectral crystal and a detector. The atomic species (element) content in the sample, atomic species analysis in the sample, and the like are then obtained from the wavelength and intensity of the X-ray spectrum. On the other hand, in the energy dispersive type, fluorescent X-rays are directly detected by a semiconductor detector, which provides an output signal pulse of pulse height value in proportion to the energy of the primary X-rays. The output signal pulse is then electrically separated for every energy of the primary X-rays by a pulse height analyzer, thereby to obtain an energy spectrum, and a sample analysis is performed from the peak of this energy spectrum.

The wavelength dispersive type has merits that an energy resolution is high, and a P/B ratio and precision of quantitative analysis are superior, whereas it has defects that a measurement time is long since the measurement is performed while moving at every constant angle. Also, the wavelength dispersive type needs a moving mechanism and precise operation such as rotation of the detector around the spectral crystal, and its analyzing apparatus is very large in size. On the other hand, since the energy dispersive type detects fluorescent X-rays directly by the semiconductor detector without using any spectral crystals or the like as described above, it can measure the X-ray spectrum of a wide range of energy at the same time. Also, the efficiency of the detector is very high, and its analyzing apparatus is small in size, so that it is very preferable in the site of research and development requiring effective use of space. However, the energy dispersive type having such superior features has a defect that an energy resolution is low as compared with the wavelength dispersive type.

Fluorescent X-rays are X-rays which are generated from each atomic species contained in a sample irradiated with primary X-rays of a certain energy or more and have energy intrinsic to each atomic species. Thus, by comparing the intensity of fluorescent X-rays from a certain atomic species with that of fluorescent X-rays from another atomic species, the content ratio of the atomic species in the sample can be obtained. However, in spite of the feature that the fluorescent X-rays originally have dispersion of a very narrow width with respect to the energy, they are observed as a peak having a large width because of the capacity of the detector (circuit) decomposing the received energy and because of other uncertain factors. Therefore, since the width of the peak is widened, there have been problems that although integration intensities of every independent peaks ought to be obtained in the case where the peak energies of the respective atomic species in the sample are widely separated from one another, the peaks overlap with one another so that it becomes difficult to obtain a separated intensity ratio, and also in the case where the peaks have energies close to one another, an overlapping portion is originally produced to some degree, but the overlapping portion becomes further remarkable. Especially, the energy dispersive type is inferior to the wavelength dispersive type in capacity of separating adjacent peak energies from each other, thus overlapping occurs more remarkably than the wavelength dispersive type, and the energy resolution is low.

Then, in order to compensate lowering of analyzing precision caused by such low energy resolution, a technique called profile fitting (or whole pattern fitting) is often used.

This profile fitting is one of methods of extracting a physical quantity from data having a peak-shaped signal. In the fluorescent X-ray analyzing method, with respect to a sample to be analyzed, a spectrum of each atomic species to be measured is simulated in advance, and fitting of the simulated spectrum with respect to an measured energy spectrum is performed, so that a content ratio of an atomic species having the simulation spectrum matched with the measured energy spectrum, and the like are obtained.

Here, the profile fitting in the fluorescent X-ray analyzing method will be further described.

In the profile fitting, in order to simulate an energy spectrum of a single atomic species in advance, it is necessary to introduce not only physical parameters but also simulation parameters to all conceivable error factors such as mechanical, electrical, and geometrical factors. Then, values of parameters at which the result of the simulation is closest to measurement values are determined by the least square method. However, with respect to a fine shape of each peak, the influence from a mechanical and electrical system is large, and there is a possibility that the shape changes for each apparatus and also changes with time. Thus, it is very difficult to accurately simulate all energy spectra of which the shapes change like this. Accordingly, a simulation spectrum is replaced by a function which relatively simply expresses an energy profile, a so-called profile function, thereby attempting to express various profile shapes by parameter values of the profile function.

FIG. 1 shows an example of an energy spectrum symmetrical with respect to a peak position. Here, the profile function is made P (param;e) as a function searching for a parameter group (param) which is for expressing an energy profile and an intensity of energy (e).

A simplest example of a profile analysis relates to one energy peak. In this case, parameters are a position e, of the peak and scale factor s. This is, as indicated in Eq.1, by setteing a profile function at some position and multiplying the whole with the scale factor s, the energy spectrum $I_{(e)}$ of the single peak can be expressed.

$$I_{(e)} = S \cdot P_{(param, e-t_0)} \tag{Eq.1}$$

Then, the peak position and the value of the scale factor, together with the parameters of the profile function, are changed to search for values matching the actual peak. FIG. 2 shows an example of this single peak fitting (in the drawing, "residual" indicates an error between a measured value and a calculated value). Further, when the integral value of the profile function is 1, the scale factor itself expresses an integration intensity. In the case where there are two peaks as exemplified in FIG. 3, two profile functions, each having own scale factor and peak position, are prepared, and all parameters are to be matched. Then, the respective scale factors become "separated integration intensity". Even if peaks are further increased, the same is true, and this can be expressed by Eq. 2.

$$I_{(e)} = S_1 \cdot P_{(param;e=e_1)} + S_2 \cdot P_{(param,e=e_2)} + \quad (Eq.2)$$

However, there occur such problems that when parameters increase, it becomes difficult to obtain an answer. Thus, it becomes important to study the feature of fluorescent X-rays carefully and estimate what is known and what can be eliminated from the parameters. First, a fluorescent X-ray which is energy emitted from a certain atomic species has a specified value which never changes. This means that the peak position needs not to be changed. In addition, the number of fluorescent X-rays emitted from one atomic species is definite, and the ratio of intensities does not change at every measurement. Thus, the energy and relative intensity can be prepared as a table. Thus, the energy and relative intensity can be prepared as a table. Based on these features, it is preferable to decrease the number of parameters to the utmost.

First, a spectrum caused from one atomic species is considered. Based on a table of energy $e_{j,k}$ of a fluorescent X-ray k of a certain atomic species j and relative intensity $I_{j,k}$, a spectrum $I_{j(e)}$ is prepared by assigning a profile function to each peak. This can be expressed by Eq.3, and FIG. 4 shows an example of a spectrum from a single atomic species prepared in this way.

$$I_{j(e)} = \sum_{k}^{peak} I_{j,k} \cdot P_{(param;e=e_{j,k})} \quad (Eq. 3)$$

Here, it is assumed that the peak shapes are the same for all peaks, and only one parameter set of a profile is defined in common (it is defined in common also among atomic species). Parameter sets are prepared for all atomic species needed to be analyzed, and a scale factor $s_j$ for each atomic species is defined, and this is made a parameter as in Eq.4. FIG. 5 shows an example of superposition of spectra $I_{(e)}$ obtained from Eq.4 for spectra from two atomic species.

$$I_{(e)} = \sum_{j}^{atom} s_j \cdot I_{j(e)} \quad (Eq. 4)$$

Thus, it is the scale factor $s_j$ of each atomic species and the parameter as to the profile that to be optimized. And, the ratio of the scale factor becomes the ratio of integration intensity for each atomic species as it is.

In the foregoing profile fitting, Gaussian function and Lorentz function are conventionally used as the profile function P(param;e). As exemplified by Eqs. 5a and 5b and FIG. 6, the Gaussian function attenuates quickly, while the Lorentz function on has its skirts extending over a wide range. A parameter in those functions is a full width at half maximum intensity W.

Gaussian function $$P_{(W;e)} = \exp\left[-4\left(\frac{e}{W}\right)^2\right] \quad (Eq. 5a)$$

Lorentz function $$P_{(W;e)} = \left[1 + 4\left(\frac{e}{W}\right)^2\right]^{-1} \quad (Eq. 5b)$$

There are also known functions having properties of a combination of these two functions. There can be expressed as Eqs.6a and 6b, and are called pseudo-Voight function and Peason VII function. These functions uses a ratio R of contribution of the Gaussian function and the Lorentz function as a parameter, and can express an energy profile having a intermediate shape between the Gaussian function and the Lorentz function as is exemplified in FIG. 7 (in the drawing, it is depicted as "MIXED FUNCTION").

psuedo-Voigt function $$P_{(W,R;e)} = (1-R) \cdot \left[1 + 4\left(\frac{e}{W}\right)^2\right]^{-1} + R \cdot \exp\left[-4\left(\frac{e}{W}\right)^2\right] \quad (Eq. 6a)$$

Peason VII function $$P_{(W,R;e)} = \left[1 + 4\left(2^{\frac{1}{R}} - 1\right)\left(\frac{e}{W}\right)^2\right]^{-R} \quad (Eq. 6b)$$

However, all these conventional profile functions express energy profiles symmetrical with respect to the peak positions (that is, a profile in which a low energy side and a high energy side become symmetrical with respect to the peak position). Consequently, in the conventional sample analysis, although analysis precision is high for an atomic species generating a fluorescent X-ray of a symmetrical energy spectrum having a symmetrical shape with respect to the peak position, analysis precision is extremely low for an atomic species generating a fluorescent X-ray of asymmetrical energy spectrum having an asymmetrical shape with respect to the peak position since fitting to the asymmetrical energy spectrum has naturally a large error. Thus, a satisfactory analysis result can be obtained only for a sample which is predicted to have only atomic species generating fluorescent X-rays of symmetrical energy spectra. This prevents the improvement of the analysis precision and the degree of freedom in the fluorescent X-ray analyzing method, especially in the energy dispersive type.

SUMMARY OF THE INVENTION

In view of the foregoing, it is the main object of the present invention to provide a new fluorescent X-ray analyzing method and an apparatus thereof which can perform a superior quantitative and qualitative analysis even for an atomic species generating a fluorescent X-ray of an asymmetrical energy spectrum, and can remarkably improve the analysis precision and the degree of freedom of a fluorescent X-ray analysis.

BRIEF DESCRIPTION OF THE DRAWINGS

The foregoing and other objects, features and advantages of the present invention will be better understood from the following detailed description, taken in conjunction with the accompanying drawings, in which.

DETAILED DESCRIPTION OF THE INVENTION

Functions expressed by Eqs.7 and 8 can be used as asymmetrical profile functions in the present invention.

$$P_{(W,A,R_{low},R_{high};e)} = \begin{cases} (1-R_{low}) \cdot \left[1 + \left(1+\frac{1}{A}\right)^2 \left(\frac{e}{W}\right)^2\right]^{-1} + \\ R_{low} \cdot \exp\left[-\left(1+\frac{1}{A}\right)^2 \left(\frac{e}{W}\right)^2\right] \cdots e < 0 \\ (1-R_{high}) \cdot \left[1 + (1+A)^2 \left(\frac{e}{W}\right)^2\right]^{-1} + \\ R_{high} \cdot \exp\left[-(1+A)^2 \left(\frac{e}{W}\right)^2\right] \cdots e \geq 0 \end{cases} \quad \text{(Eq. 7)}$$

$$P_{(W,A,R_{low},R_{high};e)} = \quad \text{(Eq. 8)}$$

$$\begin{cases} \left[1 + \left(1+\frac{1}{A}\right)^2 \left(2^{\frac{1}{R_{low}}} - 1\right)\left(\frac{e}{W}\right)^2\right]^{-R_{low}} \cdots e < 0 \\ \left[1 + (1+A)^2 \left(2^{\frac{1}{R_{high}}} - 1\right)\left(\frac{e}{W}\right)^2\right]^{-R_{high}} \cdots e \geq 0 \end{cases}$$

The asymmetrical profile function of Eq.7 (hereinafter referred to as a split type pseudo-Voight function) is a function in which an asymmetrical factor is introduced to the foregoing pseudo-Voight function of Eq.6a and the asymmetrical profile function of Eq.8 (hereinafter referred to as a dispersion type Peason VII function) is a function in which an asymmetrical factor is introduced to the Peason VII function of Eq.6b, in consideration of characteristics of asymmetrical energy spectra of fluorescent X-rays from various atomic species. Both functions can express both of symmetrical and asymmetrical energy profiles with the value of the asymmetrical factor as a parameter.

Further, in these functions, a ratio R (also called a mixture ratio) of contribution of the Gaussian function and the Lorentz function is separately defined at a low energy side and a high energy side of an energy profile (which generally become the left side and the right side of the peak center, respectively) as Rlow and Rhigh. Accordingly, the function introducing Rlow and the function introducing Rhigh can be suitably used as to the low energy side and the high energy side, respectively, and the full width of half maximum intensity W and the ratio Rlow or Rhigh are optimized as well as the asymmetrical factor, so that it is possible to express an energy profile more accurately corresponding to right and left shapes, thereby improving the degree of freedom of the profile fitting and the precision.

Figure 1:
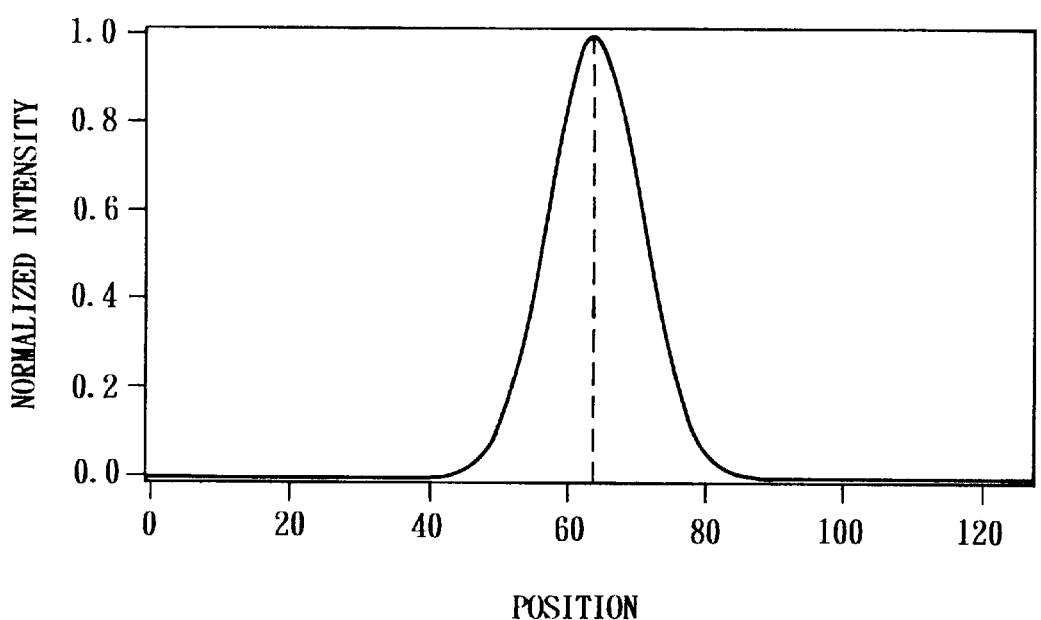
FIG. 1 is a view showing an example of a symmetrical energy spectrum.
Figure 2:
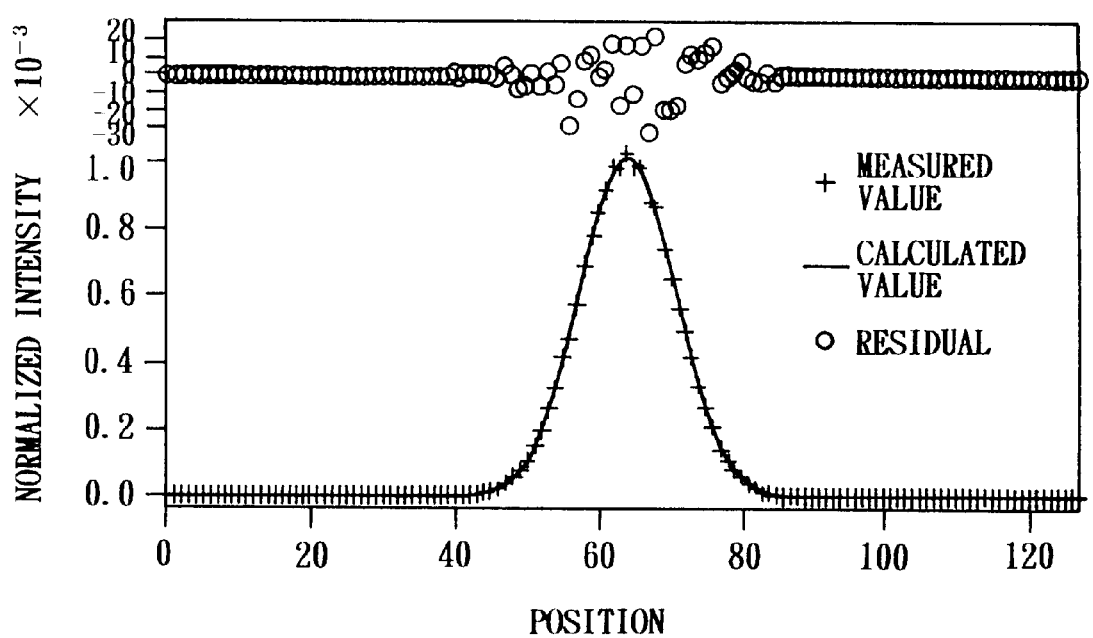
FIG. 2 is a view showing an example of profile fitting to a symmetrical energy spectrum of a single peak.
Figure 3:
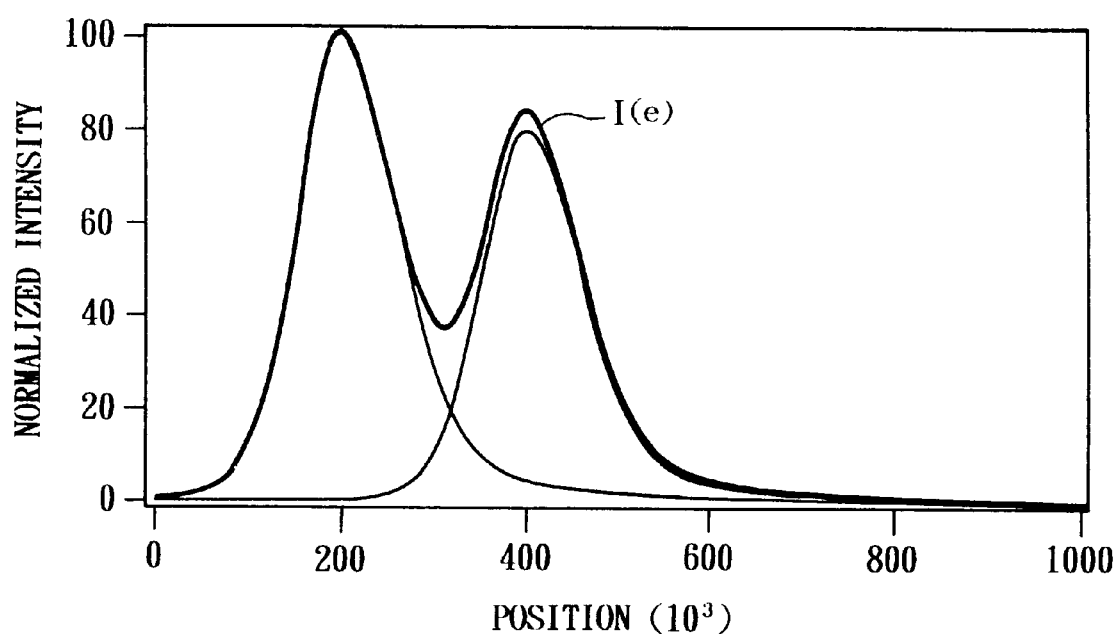
FIG. 3 is a view showing an example of two overlapping peaks.
Figure 4:
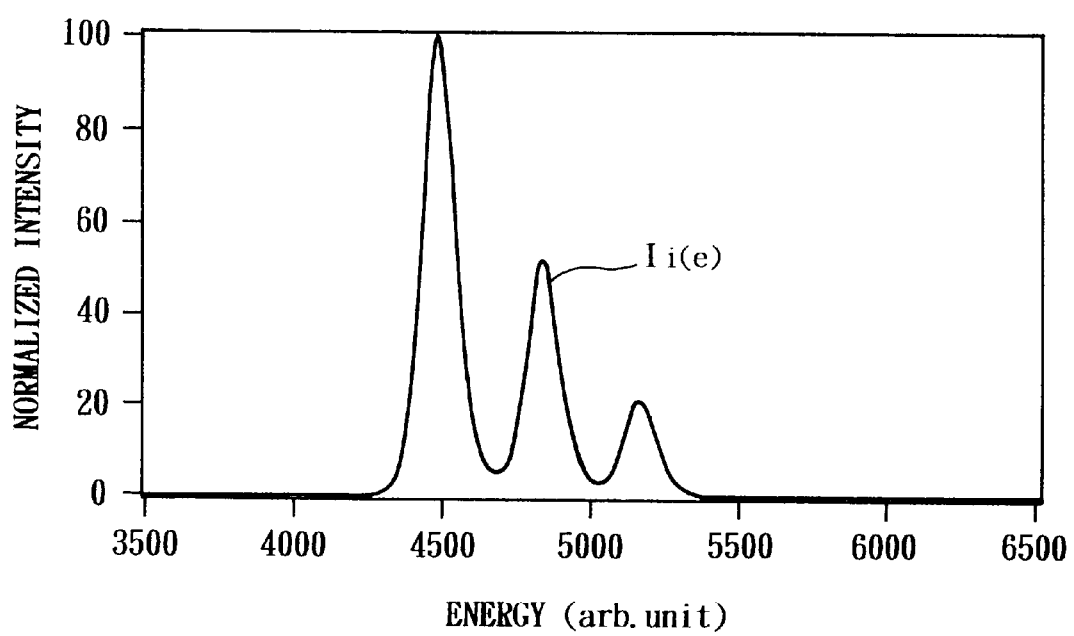
FIG. 4 is a view showing an example of an energy spectrum from a single atomic species.
Figure 5:
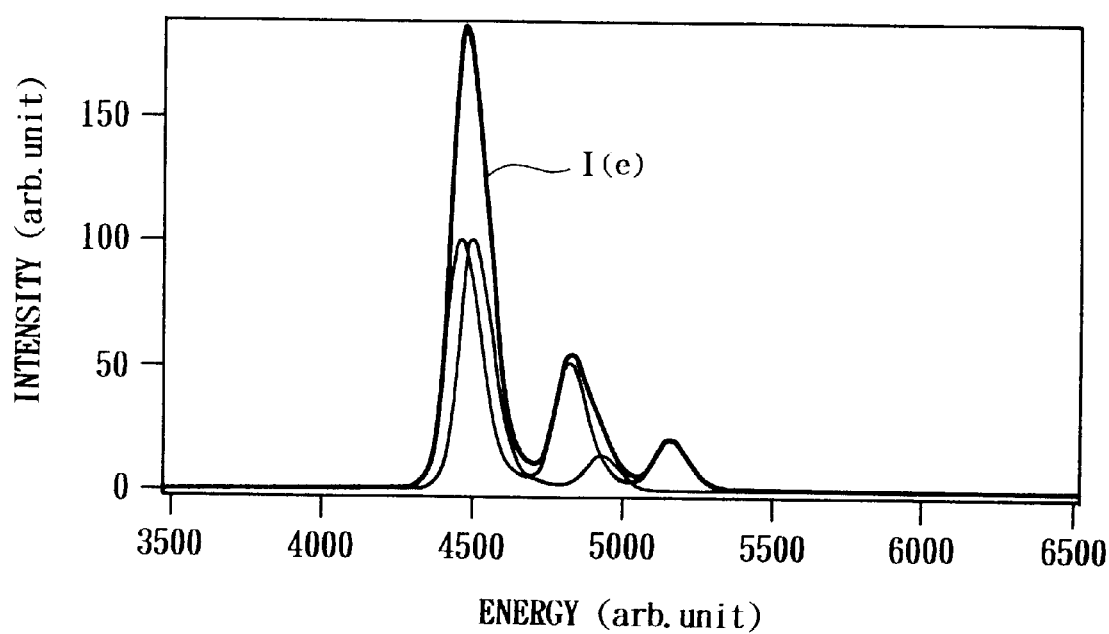
FIG. 5 is a view showing an example of superposition of energy spectra from top atomic species.
Figure 6:
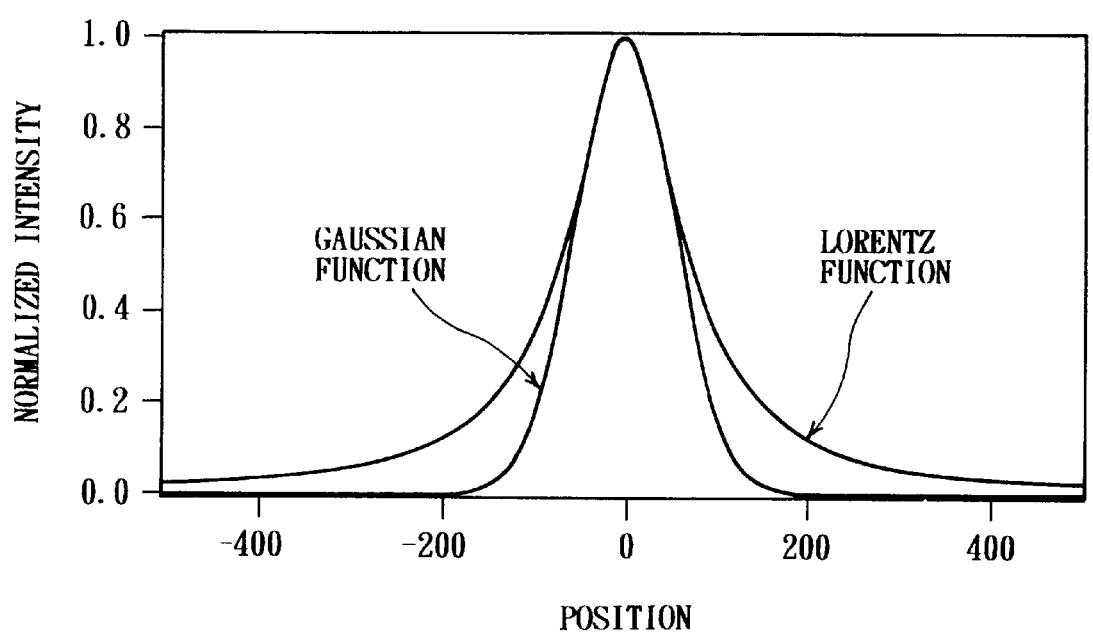
FIG. 6 is a view showing an example of profiles by the Gaussian function and the Lorentz function.
Figure 7:
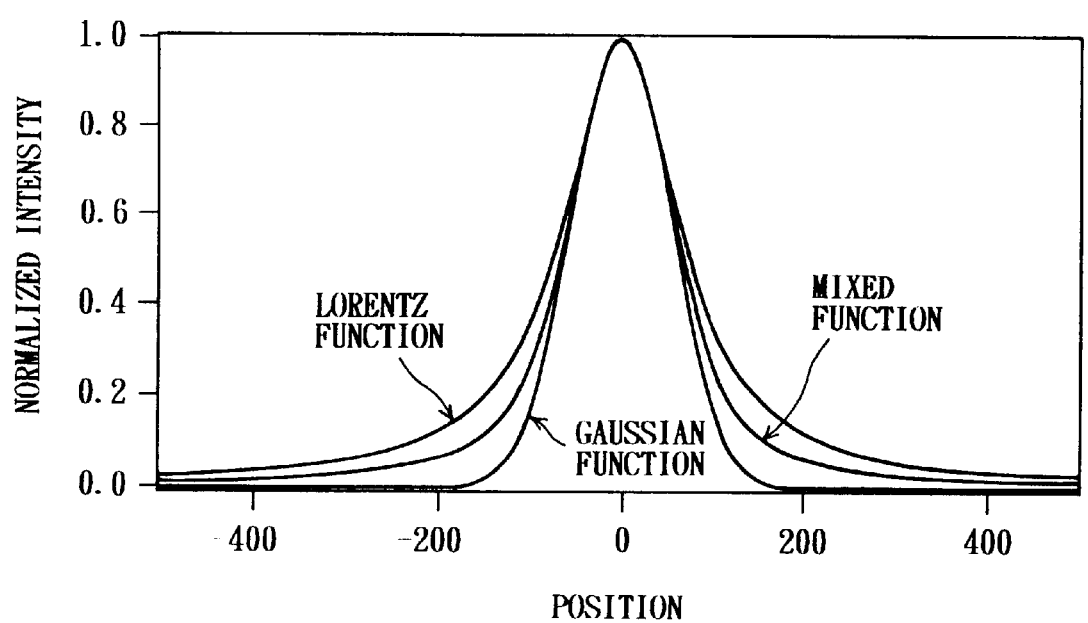
FIG. 7 is a view showing an example of a profile by the mixed function of the Gaussian function and the Lorentz function.
Figure 8:
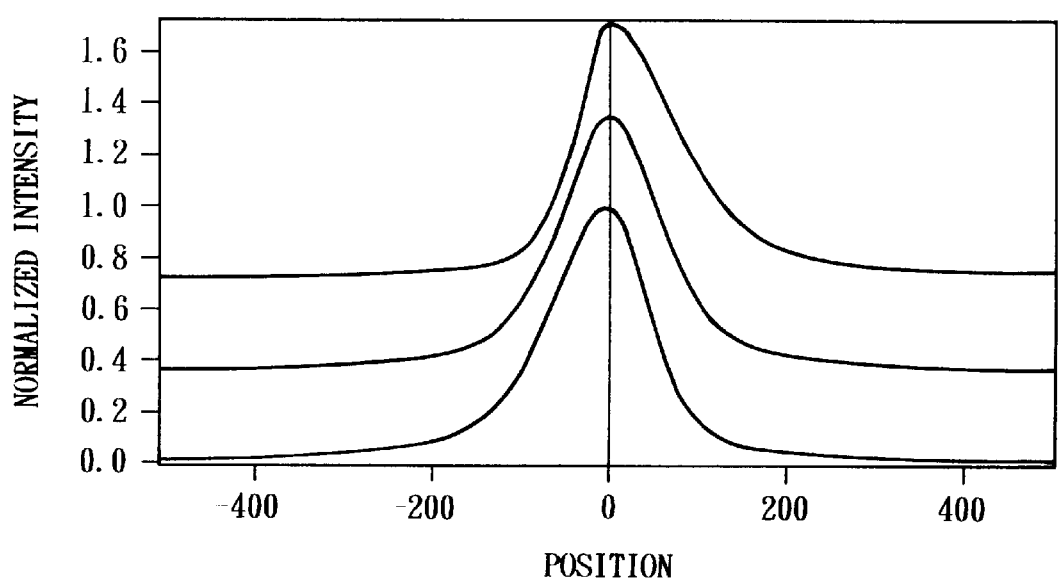
FIG. 8 is a view showing an example of profiles by asymmetrical profile functions of the present invention.

The asymmetrical factors in the asymmetrical profile functions of Eqs.7 and 8 are $(1+1/A)^2$ in the low energy side function and $(1+A)^2$ in the high energy side function. The value of each asymmetrical factor is changed by changing the value of a variable A. For example, when the variable A is 1, the asymmetrical factor becomes 4 to express the symmetrical energy profile, and when the variable A is not 1, the asymmetrical factor can express the asymmetrical energy profile. Therefore, the profile function has extremely high multipurpose properties. It is possible to perform the profile fitting with sufficient precision even to asymmetrical energy spectra of various asymmetrical shapes, not to mention the symmetrical energy spectrum, and realize an analysis with much more various purposes and easy handling. FIG. 8 shows an example of asymmetrical energy profiles expressed by such asymmetrical profile functions of the present invention. The low energy side and the high energy side have different shapes.

In actual measurement of an energy spectrum, in addition to the resolving power of the detector (or measuring device), uncertain factors are further included. The first is energy precision of the detector. Since the energy detected by the detector is often determined by setting of the gain and offset of the detector, it is necessary to correct the energy of fluorescent X-rays by a primary expression. Further, it is necessary to correct a background as well in consideration of the influence of a measurement method, environment, and the like.

In the present invention, in order to make such correction possible, a background is defined as primary expression with respect to the energy of fluorescent X-rays and is applied to the foregoing asymmetrical profile functions. This improves the precision of profile fitting further.

Eq.9 shows an example of the relation between energy $e'_{j,k}$ of fluorescent X-rays and background $b_{(e)}$. The spectrum function in which Eq.9 is applied to the asymmetrical profile function can be expressed as Eq.10.

$$\begin{cases} e'_{j,k} = shift1 \cdot e_{j,k} + shift2 \\ b_{(e)} = back1 \cdot e + back2 \end{cases} \quad \text{(Eq. 9)}$$

$$\begin{cases} I_{j(e)} = \sum_k^{peak} I_{j,k} \cdot P_{(param;e=e'_{j,k})} \\ I_{(e)} = \sum_j^{atom} s_j \cdot I_{j(e)} + b_{(e)} \end{cases} \quad \text{(Eq. 10)}$$

In this case, parameters for optimization in the profile fitting are (1) a parameter group as to the profile (param),
(2) a scale factor for each atomic species ($s_{j,k}$),
(3) a parameter as to an energy shift (shift1, shift2), and
(4) a parameter as to the background (back1, back2).

In addition, for optimization, there is required a table of energy $a_{j,k}$ of fluorescent X-rays for each atomic species and relative intensity $I_{j,k}$. Such a table ($e_{j,k} \rightarrow I_{j,k}$) will be called a fluorescent ray table.

Asymmetry tends to occur more with characteristics of an apparatus than those of a sample itself. For example, even in the same measurement/detection apparatus, the asymmetry changes with an installation place, was frequency, readjustment, and the like. Thus, in the prior art having only a symmetrical profile function, it has been necessary to measure a standard sample at every measurement of fluorescent X-rays and prepare a database in order to absorb these uncertain factors. On the other hand, as described above, the present invention realizes the profile function which can sufficiently absorb the uncertain factors of asymmetry due to the apparatus and has a great degree of freedom to express profile. As a result, an individual difference of apparatuses of the same kind can be completely absorbed, and even in the different kinds of apparatuses, the uncertain factors can be sufficiently absorbed such that the remeasurement of a standard sample at every measurement of fluorescent X-rays as in the prior art becomes unnecessary, and by merely preparing the database of energy and relative intensity, which can be predicted physically, as the fluorescent ray table, it is possible to measure fluorescent X-rays without measuring the standard sample. Thus, profile fitting with superior precision and multipurpose properties can be easily performed.

Furthermore, in the present invention, a fundamental parameter method (hereinafter referred to as an FP method) may be combined with the profile fitting in order to further improve the precision of the profile fitting using the foregoing asymmetrical profile function. The fluorescent ray table of the intensity ratio (or relative intensity) of fluorescent rays emitted from atomic species is prepared by using the FP method, and then the foregoing profile fitting is performed using this table.

Further, since it is difficult to obtain a satisfactory solution by only one fitting the due to characteristic of equations of the FP method, it is preferable to make a regression analysis incorporating the profile fitting.

More specifically, the FP method and the regression analysis incorporating the profile fitting are performing as described below. The following explanation relates to analyzing of a composition ratio of a material sample made of known atomic species.

Figure 9:
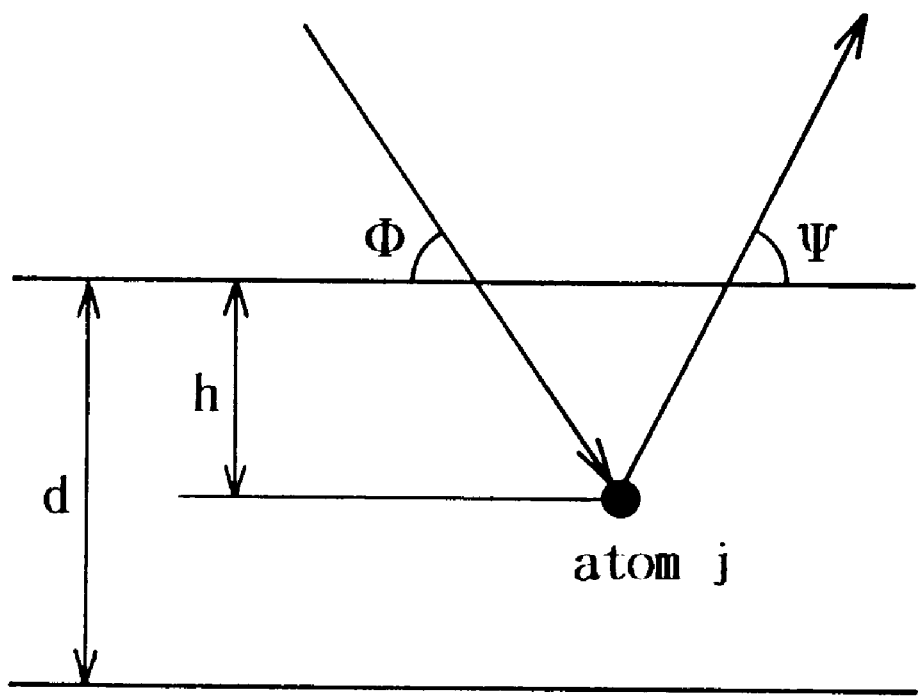
FIG. 9 is a conceptual view showing an example of a measurement optical system.

First, a simple example of the FP method will be described in the case where an excitation source is a monochromatic X-ray and a sample to be analyzed is a bulk single crystal. An intensity of the monochromatic X-ray at a bulk surface is $I_o$ and its energy is $e_o$ (keV). An thickness of the crystal is d (cm). FIG. 9 shows an example of an optical system in this case. An incident angle of an excitation beam is $\phi$(rad), and a fluorescent ray of an outgoing angle $\Psi$(rad) is observed.

First, a fluorescent ray from an atomic species j existing at a depth of h (cm) as exemplified in FIG. 9 is considered. The intensity of the excitation beam irradiated to the atomic species j can be given by Eq.11.

$$I_A = I_0 \exp\left(-\mu_{(e_0)} \cdot \frac{h}{\sin\Phi}\right) \quad \text{(Eq. 11)}$$

Here, $\mu(e)$(1/cm) is a linear absorption coefficient of the bulk crystal with respect to the energy a (keV). The intensity of k-th fluorescent ray emitted from the atomic species j by this excitation ray can be expressed per unit volume by Eq.12.

$$I_B = I_A \cdot \rho \cdot Q_{j,k} \quad \text{(Eq.12)}$$

Here, $\rho$(g/cm$^3$) denotes a density of the bulk crystal, and $Q_{j,k}$ denotes a generation efficiency of the k-th fluorescent ray of the atomic species j. $Q_{j,k}$ is given as Eq.13.

$$Q_{j,k} = \frac{\mu_{j(e_0)}}{\rho_j} \cdot c_j \cdot \left(1 - \frac{1}{J_j}\right) \cdot \omega_j \cdot R_k^j \quad \text{(Eq. 13)}$$

j; atomic species
k; number of fluorescent ray
$\mu_{j\ (e)}$ (1/cm); linear absorption coefficient with regard to energy e (keV)
$\rho_j$ (g/cm$^3$); density
$c_j$; composition ratio
$\omega_j$; fluorescence yield
$R_k^j$; intensity with regard to the entire fluorescent ray Here, considering the fact that all except the composition ratio are physical constants intrinsic to the material, Eq.13 can be expressed by Eq.14.

$$Q_{j,k} = c_j Q'_{j,k} \quad \text{(Eq.14)}$$

Thus, $Q'_{j,k}$ becomes an Eq.15.

$$Q'_{j,k} = \frac{\mu_{j(e_0)}}{\rho_j} \cdot \left(1 - \frac{1}{J_j}\right) \cdot \omega_j \cdot R_k^j \quad \text{(Eq. 15)}$$

Next, the intensity when this fluorescent ray reaches the surface of the bulk can be given by Eq.16

$$I_C = I_B \cdot \exp\left(-\mu_{(e_j,k)} \cdot \frac{h}{\sin\Psi}\right) \quad \text{(Eq. 16)}$$

This is the intensity of a fluorescent ray from a certain layer. The fluorescent intensity of the entire bulk can be obtained by integration in the depth direction from 0 to d as shown in Eq.17.

$$\int_0^d I_C dh \quad \text{(Eq. 17)}$$

As a result of integration, the intensity $I_{j,k}$, of the k-th fluorescent ray emitted from the atomic species j can be obtained by Eq.18.

$$I_{j,k} = I_o \cdot c_j \cdot Q'_{j,k} \cdot \rho \cdot \frac{1 - \exp\left[-\left(\frac{\mu_{(e_0)}}{\sin\Phi} + \frac{\mu_{(e_{j,k})}}{\sin\Psi}\right) \cdot d\right]}{\frac{\mu_{(e_0)}}{\sin\Phi} + \frac{\mu_{(e_{j,k})}}{\sin\Psi}} \quad \text{(Eq. 18)}$$

In the fluorescent ray intensity formula of Eq.18, prepared by the FP method as described above, including the composition ratio as a variable, a value to be determined is the composition ratio c (which expresses the set of $c_j$). Thus, considering this parameter, the above equation is further modified. First, Eq.18 contains the composition ratio $c_j$ of the atomic species j. The linear absorption coefficient of the bulk is a value calculated by Eq.19 and contains composition ratios of all atomic species.

$$\mu_{(e)} = \rho \cdot \sum_i \frac{\mu_{i(e)}}{\rho_i} \cdot c_i \quad \text{(Eq. 19)}$$

Thus, Eq.18 has very high non-linearity with respect to the composition ratio c. Here, as in Eqs.20a and 20b, $A_{j,k(e)}$ and a scale factor $s_j$ are introduced.

$$A_{j,k(e)} = Q'_{j,k} \cdot \rho \cdot \frac{1 - \exp\left[-\left(\frac{\mu_{(e_0)}}{\sin\Phi} + \frac{\mu_{(e_{j,k})}}{\sin\Psi}\right) \cdot d\right]}{\frac{\mu_{(e_0)}}{\sin\Phi} + \frac{\mu_{(e_{j,k})}}{\sin\Psi}} \quad \text{(Eq. 20a)}$$

$$S_j = I_o \cdot c_j \quad \text{(Eq.20b)}$$

The intensity of the k-th fluorescent ray emitted from the atomic species j is expressed by Eq.21, and is divided into a linear portion and a nonlinear portion with respect to the composition ratio.

$$I_{j,k} = S_j \cdot A_{j,k(e)} \quad \text{(Eq.21)}$$

Next, using Eq.21 made by modifying the fluorescent ray intensity formula as described above, the regression analysis incorporating the profile fitting is performed.

Figure 10:
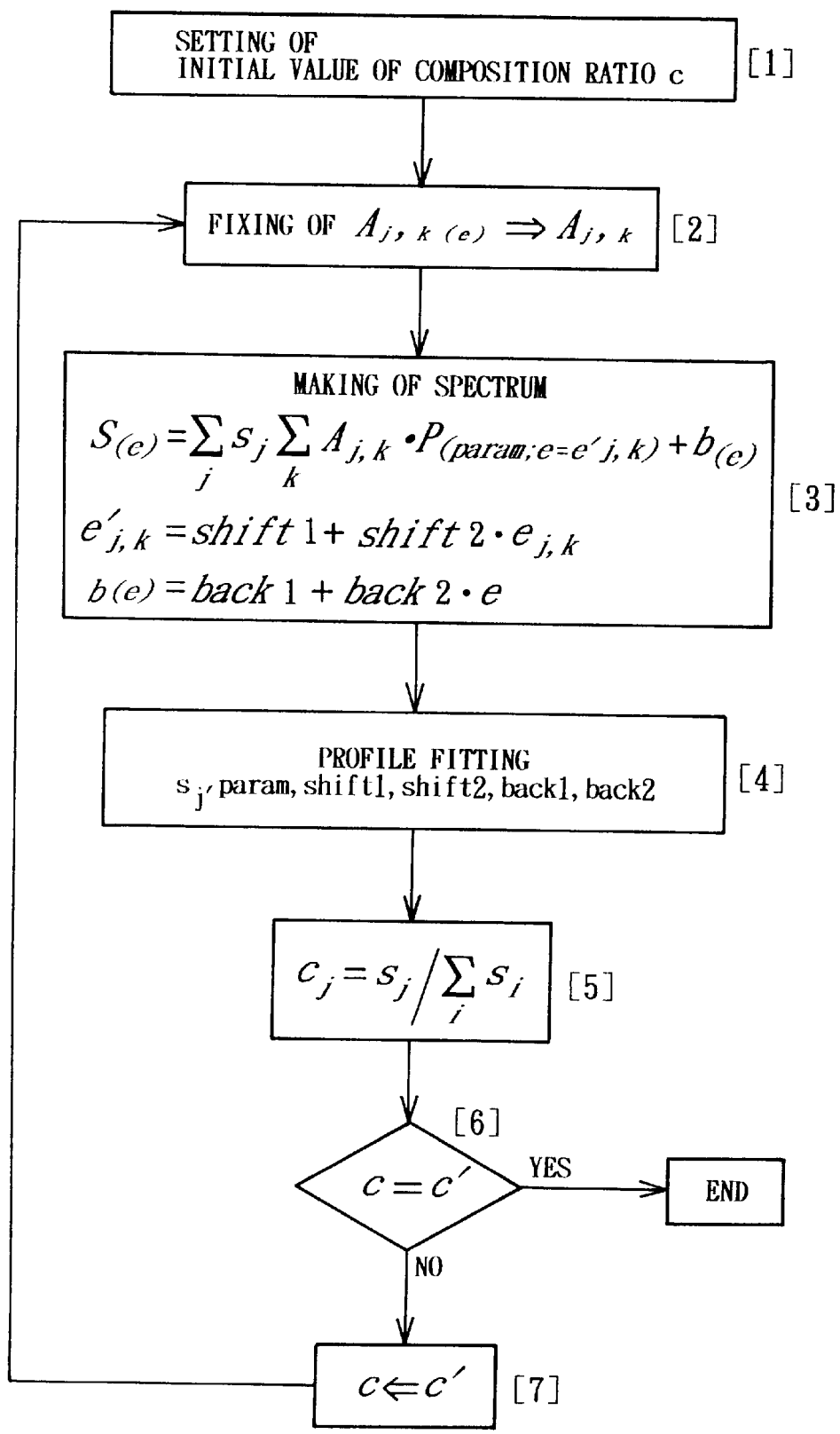
FIG. 10 is a flowchart showing steps of a regression analysis using an FP method.

FIG. 10 is a flowchart showing steps of the regression analysis.

<step [1]> An initial value of the composition ratio c of atomic species to be analyzed is assumed.

<step [2]> By using the assumed composition ratio c, $A_{j,k(c)}$ is treated as a coefficient $A_{j,k}$ independent on the composition ratio c.

<step [3]> A spectral function $S_{(e)}$, that is, a function expressing an energy profile of a sample is prepared as Eq.22.

$$S_{(e)} = \sum_j s_j \sum_k A_{j,k} \cdot P_{(param; e = e'_{j,k})} + b_{(e)} \quad \text{(Eq. 22)}$$

$$e'_{j,k} = shift1 + shift2 \cdot e_{j,k}$$

$$b_{(e)} = back1 + back2 \cdot e$$

Here, P(param;e) denotes a profile function, and param denotes a parameter group for determining a profile shape by this profile function, and e denotes an energy (keV). This spectral function $S_{(e)}$ contains corrections as to the energy shift and the background. $b_{(e)}$ is a function showing the shape of the background and has back1 and back2 as parameters, and shift1 and shift2 are parameters for obtaining an amount of shift of a peak.

<step [4]> The profile fitting to the measured energy spectrum is performed by using the above spectral function $S_{(e)}$. More specifically, the energy profile expressed by the spectral function $S_{(e)}$ is subjected to the profile fitting to the measured energy spectrum. Here, parameters are $s_j$, param, back1, back2, shift1 and shift2, and these are obtained by the least square method.

<step [5]> By Eq.23, a composition ratio $c'_j$ is calculated from an objected scale factor $s_j$.

$$c_j = \frac{s_j}{\sum_i s_i} \quad \text{(Eq. 23)}$$

<step [6]> An initial value of the composition ratio, which is the composition ratio c at the time o the start used in the definition of $A_{j,k}$, is compared with a calculated value of the composition ratio, which is the composition ratio c' obtained by the profile fitting. If both are identical to each other, the analysis is ended ([6] Yes→END). In this case, the calculated value (c=c') of the composition ratio is the composition ratio of the sample to be obtained. If both are not identical to each other, the procedure proceeds to a next step [7] ([6] No→[7]).

<step [7]→[2]> The composition ratio c is replaced by c', and the procedure returns to the step [2]. Then, the foregoing steps are repeated until $c_j$=c'.

By performing the double regression analysis as described above, the composition ratio c of the atomic species j constituting the sample can be obtained more precisely and more easily.

In the case where secondary excitation occurs when a secondary fluorescent ray is generated from the atomic species by the primary fluorescent ray, the influence of this secondary fluorescent ray may become so large that it can not be neglected. Thus, in the foregoing profile fitting, a correction of the secondary fluorescent ray can be made. This correction can be divided into a linear portion and a nonlinear portion like the absorption correction, and thus can be realized by performing the regression analysis similar to the above.

Figure 11:
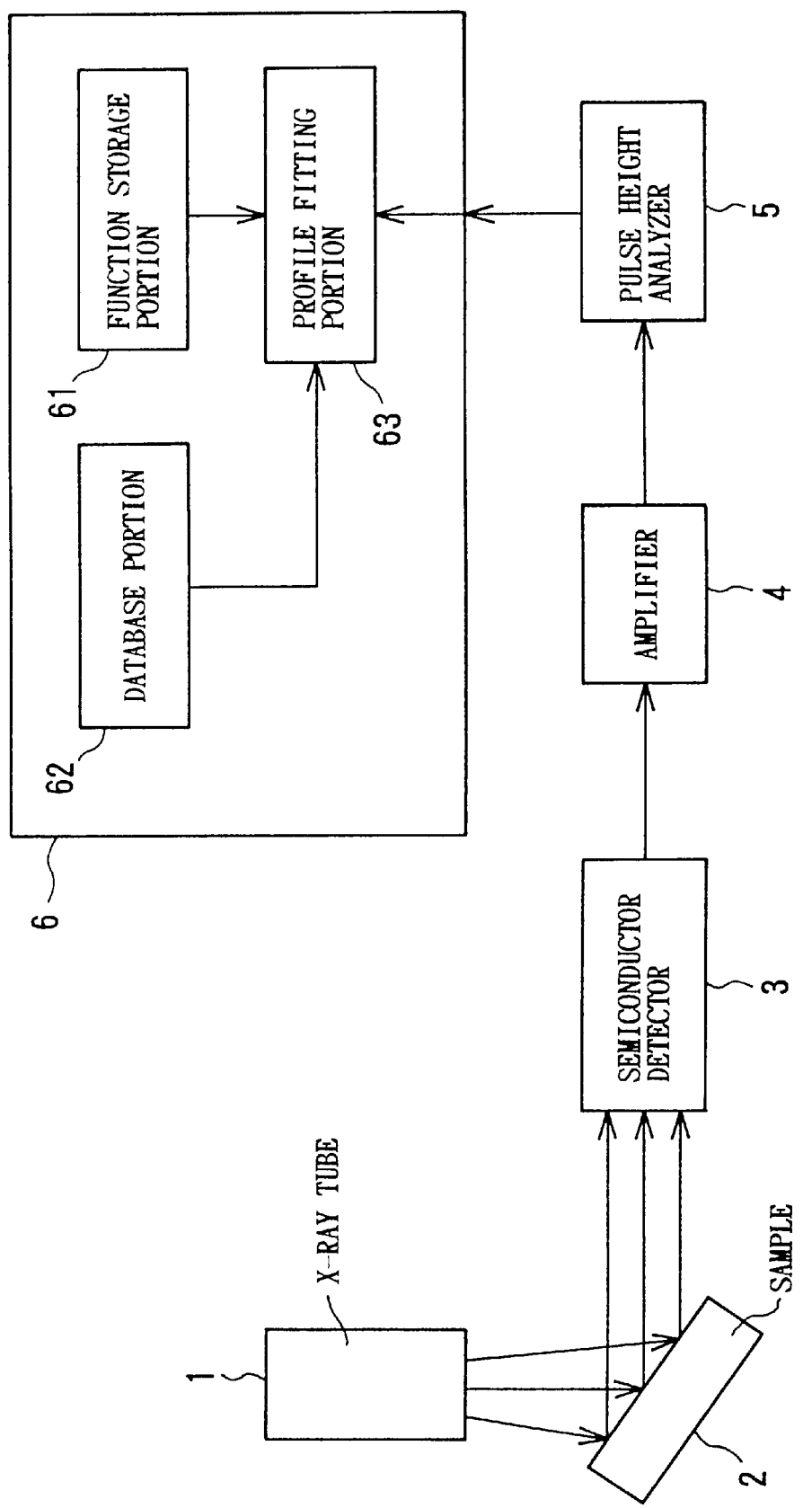
FIG. 11 is a block diagram illustrating a fluorescent X-ray analyzing apparatus of the present invention.

FIG. 11 is a block diagram illustrating an embodiment of a fluorescent X-ray analyzing apparatus which uses the method of the present invention. In FIG. 11, reference numeral 1 designates an X-ray tube; 2, a sample; 3, a semiconductor detector; 4, an amplifier; 5, a pulse height analyzer; and 6, a computer. The profile fitting of the fluorescent X-ray analyzing method of the present invention is executed by the computer 6. The computer 6 for analyzing the sample 2 can use the asymmetrical profile function $P_{(W, A, Rlow, Rhigh; e)}$ of Eqs.7 and 8 and the symmetrical profile function $P_{(W; e)}$ of Eq.5, among which one function is selected for profile fitting of the energy spectrum of the fluorescent X-rays measured by the semiconductor detector 3 and obtained through the amplifier 4 and the pulse height analyzer 5.

More specifically, for example, this computer 6 includes, as computer software, a function storage portion 61 for storing the asymmetrical profile function and the symmetrical profile function, a database portion 62 for storing a fluorescent ray table of energy and relative intensity of fluorescent X-rays for each atomic species as a database, and a profile fitting portion 63 for performing profile fitting by using the asymmetrical or symmetrical profile function from the function storage portion 61 and the fluorescent ray table from the database portion 62. Since there are normally several kinds of fluorescent X-rays from one kind of atomic species and each appears with a specified intensity ratio at the same time, the fluorescent ray table stored in the database portion 62 includes the energy and relative intensity of each kind of the fluorescent X-rays for each atomic species. In the foregoing respective equations, each atomic species is indicated by j, and each fluorescent X-ray is indicated by k. The database portion 62 and the function storage portion 61 as described above may be computer memory means.

For analyzing the composition ratio of the sample 2, such as a thin film, composed of known atomic species by this computer 6, first, the profile fitting portion 63 reads out the fluorescent ray table of each atomic species constituting the sample 2 from the database portion 62 and also the asymmetrical or symmetrical profile function from the function storage portion 61, then prepares an energy profile for each single atomic species is prepared. That is, for each single atomic species, a suitable energy profile is defined by the asymmetrical or symmetrical profile further with the peak position (expressed by an energy value) and the relative intensity of each kind of fluorescent X-rays exhibited in the fluorescent ray table, and further, these respective energy profiles are convoluted, so that an energy profile $I_{j(e)}$ for each single atomic species is prepared (see Eq.3; $P_{(param;\ e)}=P_{(W,\ A,\ Rlow,\ Rhigh;\ e)}$ or $P_{(w;\ e)}$). Next, an expected composition ratio is defined as a scale factor $s_j$, by which the energy profile $I_{j(e)}$ of each single atomic species is multiplied, and those are overlapped, so that the energy (hereinafter referred to as a mixed profile) of the sample 2 is prepared (see Eq.4). Then, until this mixed profile coincides with the measured spectrum (that is, until an error between both becomes within a desired range), fitting is repeated by changing the function parameters and the composition ratio, and when both finally coincide with each other, the composition ratio becomes the desired composition ratio.

Further, in the computer 6, a background which is a primary expression with respect to the energy may be introduced, and a shift amount which is a primary expression with respect to the energy may also be introduced, so that corrections can be made with respect to the energy of the fluorescent X-rays and the background. Specifically, the foregoing Eqs. 9 and 10 are used, and in the profile fitting, [1] the parameter group (param) as to the profile, [2] the scale factor ($s_{j,k}$) of each atomic species, [3] the parameter (shift1, shift2) as to the energy shaft, and [4] the parameter (back1, back2) as to the background are optimized.

Additionally, in this fluorescent X-ray analyzing apparatus, although the profile fitting may be performed by using only the asymmetrical profile function, in order to make the degree of freedom of analysis higher, it is preferable that both the asymmetrical profile function and the symmetrical profile function can be used and suitably selected as described above.

As an example, a composition ratio analysis of a mixture of barium Ba/titanium Ti was performed by this fluorescent X-ray analyzing apparatus of the present invention, and this will be described below.

As the semiconductor detector 3, an SI-PIN was used. As the excitation source, an Lβ line (9.7 keV) of W was used. In the excitation by the Lβ line of W, fluorescent rays of L series of Ba and K series of Ti are generated (BaK absorption edge: 32.7 keV, BaL absorption edge: 6 keV, TiK absorption edge: 5 keV). Thus, a fluorescent ray table of these is prepared. The fluorescent ray table is previously stored in the database portion 62 of the computer 6 (of course, if it is not stored in the database portion 62, it may be inputted at the time of the analysis). The following table 1 and table 2 show an example of a BaL series fluorescent ray table and a TiK series fluorescent ray table, respectively.

TABLE 1

BaL series fluorescent ray table

| Label | Energy (keV) | Relative intensity |
|---|---|---|
| L beta3 | 4.91893 | 0.333118 |
| L gamma2,3 | 5.7982 | 0.0506699 |
| L gamma4 | 5.9748 | 0.00573992 |
| L gamma5 | 5.36999 | 0.0163163 |
| L beta1,4 | 4.81949 | 0.864143 |
| L gamma1 | 5.52959 | 0.0648983 |
| L tau | 3.93647 | 0.0191909 |
| L beta6 | 4.98689 | 0.0274759 |
| L alpha | 4.4543 | 1 |
| L beta2 | 5.15077 | 0.262916 |

TABLE 2

TiK series fluorescent ray table

| Label | Energy (keV) | Relative intensity |
|---|---|---|
| K alpha | 4.49502 | 1 |
| K beta1 | 4.9001 | 0.0860339 |
| K beta2 | 4.9288 | 0.0846468 |

First, as described above, by using these fluorescent ray tables, the energy profile $I_{j(e)}$ of each of Ba and Ti is prepared by Eqs.9 and 10. As the profile function P(param;e), the dispersive type pseudo-Voigt function of Eq.7 was used. Next, the energy profile $I_{j(e)}$ of each of Ba and Ti is multiplied by the scale factor $s_1$ which is the composition ratio, and each is added, thereby to prepare a mixed profile $I_{(e)}$. Then, [1] the parameter group (W, A, $R_{low}$, $R_{high}$) of the dispersive type pseudo-Voigt function, [2] the composition ratio (=scale factor ($s_j$) of each of Ba and Ti, [3] the parameters (shift1, shift2) as to the energy shift, and [4] the parameters (back1, back2) as to the background are searched by the least square method so that the mixed profile $I_{(e)}$ coincides with the measured energy spectrum of the fluorescent X-rays from the Ba/Ti mixture (that is, an error between both becomes within a permissible range).

Figure 12:
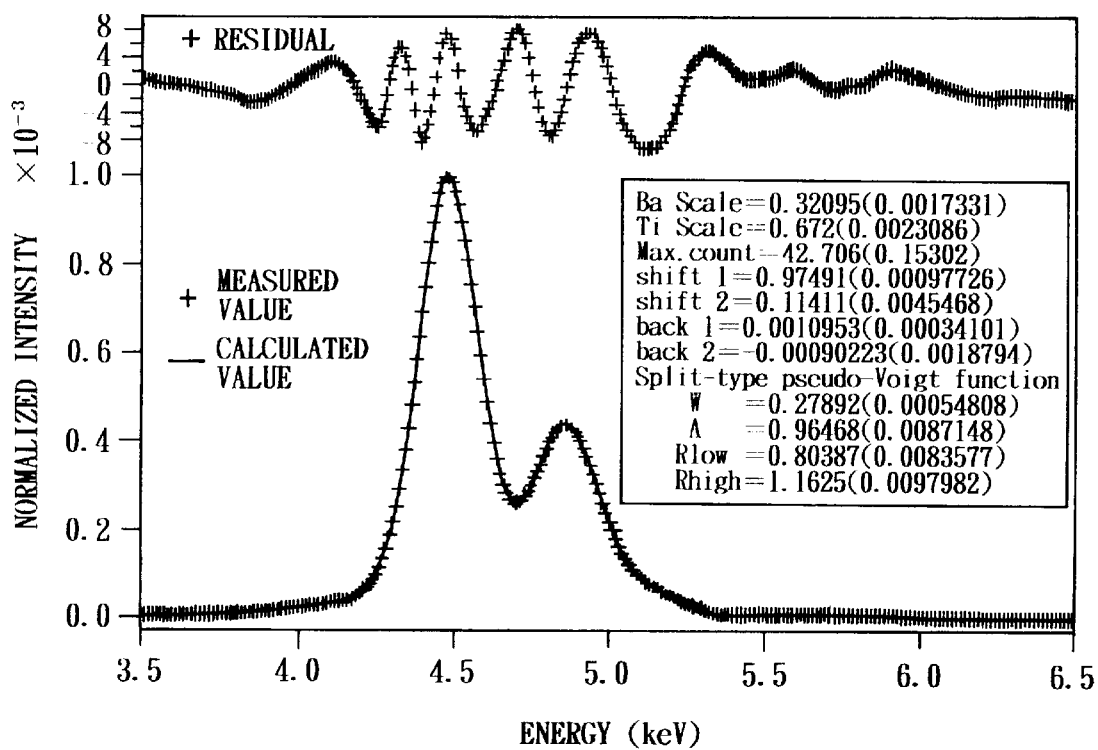
FIG. 12 is a view showing a result of profile fitting according to the present invention.

FIG. 12 shows, the measured spectrum (denoted as "measured value" in the drawing), the above mixed spectrum (denoted as "calculated value" in the drawing), the error (denoted as "residual" in the drawing), and the respective parameter values when the error becomes within the permissible range. As is apparent from FIG. 12, the mixed spectrum sufficiently fitting to the measured energy spectrum is obtained. The scale factor ("Ba Scale" in the drawing) of Ba is 0.32095 (0.0017331), the scale factor ("Ti Scale" in the drawing) of Ti is 0.672 (0.0023086), and these are the composition ratio of Ba and Ti. Other parameters are as set forth in the drawing ("Max. count"=maximum intensity in the analysis range, "shift1, shift2"=energy shift parameters shift1, shift2, "back1, back2"=background parameters back1, back2, "W"=full width at half maximum intensity W, "A"=variable A of asymmetrical factor, and "Rlow, Rhigh"=low energy side mixture ratio Rlow, high energy side mixture ratio Rhigh).

Accordingly, by the fluorescent X-ray analyzing method and apparatus of the present invention can realize, with high precision, satisfactory fitting to the measured energy spectrum of fluorescent X-rays composed of a plurality of peaks, thereby to analyze the composition ratio of the sample with high precision. The resolving capacity with respect to the measured energy spectrum, the resolution of which is poor due to superposition of the respective peaks, can be raised, and the application range of the detector can also be improved.

Further, if the foregoing FP method and the regression analysis incorporating the profile fitting are performed, the sample analysis can be realized with higher precision.

As described above in detail, according to the fluorescent X-ray analyzing method and apparatus of the present invention, a superior quantitative analysis and qualitative analysis can be performed even to an atomic species generating fluorescent X-rays of an asymmetrical energy spectrum, and regardless of symmetry or asymmetry of an energy spectrum, it is possible to realize a fluorescent X-ray analysis having a high degree of freedom, multipurpose, and easy to handle.

By the asymmetrical profile function having the high degree of freedom, it becomes possible to absorb the change due to various kinds of devices, a change of a detector with time, and a change after readjustment, thus any corrections to such changes are not necessary each time the correction is made and also frequent remeasurement of the reference intensity of each atomic species is not necessary. Consequently, it is possible to make the fluorescent X-ray analysis more easily.

Furthermore, since the peak positions and intensity ratios of a plurality of fluorescent X-rays from a single atomic species are caused by a pure physical phenomenon, if an excitation X-ray source is the same, profile fitting with high precision can be realized by using a common fluorescent ray table to various fluorescent X-ray measuring apparatuses and measuring methods. In addition, with respect to a material sample in which an absorption effect of X-rays becomes large, the application range is further widened in coordination with the FR method.

While the invention has been described in detail and with reference to specific embodiments thereof, it will be apparent to one skilled in the art that various changes and modifications can be made therein without departing from the spirit and scope thereof.

What is claimed is:

1. A fluorescent X-ray analyzing method in which fluorescent X-rays generated from a sample by irradiation of X-rays or particle beams are measured as an energy spectrum and a sample analysis is performed using the measured energy spectrum, said fluorescent X-ray analyzing method comprises:

performing profile fitting to the measured energy spectrum by using an asymmetrical profile function which can express a symmetrical and an asymmetrical energy profile in accordance with an asymmetrical factor thereof.

2. A fluorescent X-ray analyzing method according to claim 1, wherein the asymmetrical profile function is expressed by the following equation:

$$P_{(W,A,R_{low},R_{high};e)} = \begin{cases} (1-R_{low}) \cdot \left[\left[1+\left(1+\frac{1}{A}\right)^2\left(\frac{e}{W}\right)^2\right]\right]^{-1} + \\ R_{low} \cdot \exp\left[-\left(1+\frac{1}{A}\right)^2\left(\frac{e}{W}\right)^2\right] \cdots e < 0 \\ (1-R_{high}) \cdot \left[\left[1+(1+A)^2\left(\frac{e}{W}\right)^2\right]\right]^{-1} + \\ R_{high} \cdot \exp\left[-(1+A)^2\left(\frac{e}{W}\right)^2\right] \cdots e \geq 0 \end{cases}.$$

3. A fluorescent X-ray analyzing method according to claim 1, wherein the asymmetrical profile function is expressed by the following equation:

$$P_{(W,A,R_{low},R_{high};e)} = \begin{cases} \left[1+\left(1+\frac{1}{A}\right)^2\left(2^{\frac{1}{R_{low}}}-1\right)\left(\frac{e}{W}\right)^2\right]^{-R_{low}} \cdots e < 0 \\ \left[1+(1+A)^2\left(2^{\frac{1}{R_{high}}}-1\right)\left(\frac{e}{W}\right)^2\right]^{-R_{high}} \cdots e \geq 0 \end{cases}.$$

4. A fluorescent X-ray analyzing method according to claim 1, comprising the steps of:

making an energy profile of each atomic species by using the asymmetrical profile function and a fluorescent ray table of each atomic species in the sample;

making an energy profile of the sample by multiplying the energy profile of each atomic species by a predicted composition ratio of each atomic species and adding a result up; and optimizing a parameter of the asymmetrical profile function and the composition ratio such that an error between the energy profile of the sample and the measured energy spectrum falls within a desired range.

5. A fluorescent X-ray analyzing method according to claim 4, further comprising the step of correcting an energy shift and a background with respect to the energy profile.

6. A fluorescent X-ray analyzing method according to claim 1, further comprising the steps of:

making the energy profile of the sample by using the asymmetrical profile function and a fluorescent ray intensity formula prepared by a fundamental parameter method, wherein the fluorescent ray intensity formula has a composition ratio as a variable and said energy profile is made with an initial value of the composition ratio;

obtaining a calculated value of the composition ratio by performing profile fitting of said energy profile to the measured energy spectrum;

judging whether the initial value and the calculated value of the composition ratio coincide with each other; and in the case where the initial value and the calculated value do not coincide with each other, repeating making of the energy profile of the sample and obtaining of the calculated value of the composition ratio by replacing the initial value of the composition ratio with the calculated value of the composition ratio until the initial value and the calculated value coincide with each other.

7. A fluorescent X-ray analyzing method according to claim 4, further comprising the steps of:

making the energy profile of the sample by using the asymmetrical profile function and a fluorescent ray intensity formula prepared by a fundamental parameter method, wherein the fluorescent ray intensity formula has a composition ratio as a variable and said energy profile is made with an initial value of the composition ratio;

obtaining a calculated value of the composition ratio by performing profile fitting of said energy profile to the measured energy spectrum;

judging whether the initial value and the calculated value of the composition ratio coincide with each other; and in the case where the initial value and the calculated value do not coincide with each other, repeating making of the energy profile of the sample and obtaining of the calculated value of the composition ratio by replacing the initial value of the composition ratio with the calculated value of the composition ratio until the initial value and the calculated value coincide with each other.

8. A fluorescent X-ray analyzing apparatus, characterized in that a sample analysis is performed using a fluorescent X-ray analyzing method according to any one of claims 1 to 7.

9. A fluorescent X-ray analyzing apparatus according to claim 8, wherein a symmetrical profile function, together with an asymmetrical profile function, can be used, and either one of the asymmetrical profile function and the symmetrical profile function is selected as a profile function suitable for a shape of a measured energy spectrum.

10. A fluorescent X-ray analyzing method according to claim 2, comprising the steps of:

making an energy profile of each atomic species by using the asymmetrical profile function and a fluorescent ray table of each atomic species in the sample;

making an energy profile of the sample by multiplying the energy profile of each atomic species by a predicted composition ratio of each atomic species and adding a result up; and optimizing a parameter of the asymmetrical profile function and the composition ratio such that an error between the energy profile of the sample and the measured energy spectrum falls within a desired range.

11. A fluorescent X-ray analyzing method according to claim 3, comprising the steps of:

making an energy profile of each atomic species by using the asymmetrical profile function and a fluorescent ray table of each atomic species in the sample;

making an energy profile of the sample by multiplying the energy profile of each atomic species by a predicted composition ratio of each atomic species and adding a result up; and optimizing a parameter of the asymmetrical profile function and the composition ratio such that an error between the energy profile of the sample and the measured energy spectrum falls within a desired range.

12. A fluorescent X-ray analyzing method according to claim 2, further comprising the steps of:

making the energy profile of the sample by using the asymmetrical profile function and a fluorescent ray intensity formula prepared by a fundamental parameter method, wherein the fluorescent ray intensity formula has a composition ratio as a variable and said energy profile is made with an initial value of the composition ratio;

obtaining a calculated value of the composition ratio by performing profile fitting of said energy profile to the measured energy spectrum;

judging whether the initial value and the calculated value of the composition ratio coincide with each other; and in the case where the initial value and the calculated value do not coincide with each other, repeating making of the energy profile of the sample and obtaining of the calculated value of the composition ratio by replacing the initial value of the composition ratio with the calculated value of the composition ratio until the initial value and the calculated value coincide with each other.

13. A fluorescent X-ray analyzing method according to claim 3, further comprising the steps of:

making the energy profile of the sample by using the asymmetrical profile function and a fluorescent ray intensity formula prepared by a fundamental parameter method, wherein the fluorescent ray intensity formula has a composition ratio as a variable and said energy profile is made with an initial value of the composition ratio;

obtaining a calculated value of the composition ratio by performing profile fitting of said energy profile to the measured energy spectrum;

judging whether the initial value and the calculated value of the composition ratio coincide with each other; and in the case where the initial value and the calculated value do not coincide with each other, repeating making of the energy profile of the sample and obtaining of the calculated value of the composition ratio by replacing the initial value of the composition ratio with the calculated value of the composition ratio until the initial value and the calculated value coincide with each other.

14. A fluorescent X-ray analyzing method according to claim 5, further comprising the steps of:

making the energy profile of the sample by using the asymmetrical profile function and a fluorescent ray intensity formula prepared by a fundamental parameter method, wherein the fluorescent ray intensity formula has a composition ratio as a variable and said energy profile is made with an initial value of the composition ratio;

obtaining a calculated value of the composition ratio by performing profile fitting of said energy profile to the measured energy spectrum;

judging whether the initial value and the calculated value of the composition ratio coincide with each other; and in the case where the initial value and the calculated value do not coincide with each other, repeating making of the energy profile of the sample and obtaining of the calculated value of the composition ratio by replacing the initial value of the composition ratio with the calculated value of the composition ratio until the initial value and the calculated value coincide with each other.

15. A fluorescent X-ray analyzing apparatus, characterized in that a sample analysis is performed by using a fluorescent X-ray analyzing method according to claim 2.

16. A fluorescent X-ray analyzing apparatus, characterized in that a sample analysis is performed by using a fluorescent X-ray analyzing method according to claim 3.

17. A fluorescent X-ray analyzing apparatus, characterized in that a sample analysis is performed by using a fluorescent X-ray analyzing method according to claim 4.

18. A fluorescent X-ray analyzing apparatus, characterized in that a sample analysis is performed by using a fluorescent X-ray analyzing method according to claim 5.

19. A fluorescent X-ray analyzing apparatus, characterized in that a sample analysis is performed by using a fluorescent X-ray analyzing method according to claim 6.

20. A fluorescent X-ray analyzing apparatus, characterized in that a sample analysis is performed by using a fluorescent X-ray analyzing method according to claim 7.

* * * * *